(12) United States Patent
E et al.

(10) Patent No.: US 11,768,231 B1
(45) Date of Patent: Sep. 26, 2023

(54) CURRENT MEASUREMENT CIRCUIT, CURRENT MEASUREMENT METHOD AND NANOPORE SEQUENCING DEVICE

(71) Applicant: Qitan Technology Ltd., Chengdu, Sichuan (CN)

(72) Inventors: Qiang E, Sichuan (CN); Jin Wang, Sichuan (CN); Xi Hu, Sichuan (CN)

(73) Assignee: QITAN TECHNOLOGY LTD., CHENGDU, Chengdu (CN)

( * ) Notice: Subject to any disclaimer, the term of this patent is extended or adjusted under 35 U.S.C. 154(b) by 0 days.

(21) Appl. No.: 18/198,460

(22) Filed: May 17, 2023

Related U.S. Application Data

(63) Continuation of application No. PCT/CN2022/136564, filed on Dec. 5, 2022.

(30) Foreign Application Priority Data

Jan. 20, 2022 (CN) .......................... 202210063946.7

(51) Int. Cl.
*G01R 1/30* (2006.01)
*G01R 19/00* (2006.01)
(Continued)

(52) U.S. Cl.
CPC ......... *G01R 19/003* (2013.01); *C12Q 1/6869* (2013.01); *G01R 19/16504* (2013.01)

(58) Field of Classification Search
CPC .......................... G01R 19/003; G01R 19/0092; G01R 19/165; G01R 19/16504; G01R 19/16566;
(Continued)

(56) References Cited

U.S. PATENT DOCUMENTS

| 4,257,125 A * | 3/1981 | Theall, Jr. .......... H04B 10/6972 375/333 |
| 2009/0066558 A1* | 3/2009 | Ikramov ................. G01S 13/04 342/28 |

(Continued)

FOREIGN PATENT DOCUMENTS

| CN | 1245900 A | 3/2000 |
| CN | 101331402 A | 12/2008 |

(Continued)

OTHER PUBLICATIONS

Notification to Grant Patent Right for Invention dated Apr. 1, 2022 issued for Chinese Patent Application No. 202210063946.7.
(Continued)

*Primary Examiner* — Thang X Le
(74) *Attorney, Agent, or Firm* — K&L Gates LLP

(57) ABSTRACT

This application provides a current measurement circuit including: an amplification unit, configured to amplify an electrical signal from the sensor unit; a comparison unit, configured to obtain an initial pulse signal based on a voltage signal output by the amplification unit and a preset voltage; a delay unit, electrically connected to the comparison unit and configured to delay an output of the initial pulse signal to obtain a target pulse signal; a resistance unit, wherein two terminals of the resistance unit are electrically connected to an input terminal of the amplification unit and an output terminal of the delay unit respectively, and the resistance unit is configured to charge and discharge the amplification unit based on the target pulse signal; and a calculation unit, electrically connected to the delay unit and configured to calculate a target current based on the target pulse signal output by the delay unit.

15 Claims, 5 Drawing Sheets

(51) Int. Cl.
*C12Q 1/6869* (2018.01)
*G01R 19/165* (2006.01)

(58) Field of Classification Search
CPC .... G01R 19/22; G01R 19/2513; G01R 33/04; G01R 33/063; G01R 33/0017; G01R 33/072; G01R 33/0076; G01R 33/09; G01R 33/091; G01R 33/093; G01R 33/098; G01R 31/50; G01R 31/52; G01R 31/56; G01R 31/2617; G01R 31/2827
See application file for complete search history.

(56) References Cited

U.S. PATENT DOCUMENTS

| | | | |
|---|---|---|---|
| 2009/0167247 A1* | 7/2009 | Bai | H02J 7/0016 320/134 |
| 2012/0187963 A1 | 7/2012 | Chen | |
| 2021/0226596 A1* | 7/2021 | Chen | H03M 3/432 |
| 2021/0351697 A1 | 11/2021 | Tyagi et al. | |
| 2022/0255415 A1* | 8/2022 | Ishibashi | H02M 1/0009 |

FOREIGN PATENT DOCUMENTS

| | | |
|---|---|---|
| CN | 101963629 A | 2/2011 |
| CN | 107850630 A | 3/2018 |
| CN | 109946504 A | 6/2019 |
| CN | 110945772 A | 3/2020 |
| CN | 112649661 A | 4/2021 |
| CN | 112795476 A | 5/2021 |
| CN | 112924745 A | 6/2021 |
| CN | 113489464 A | 10/2021 |
| CN | 113631925 A | 11/2021 |
| CN | 215340043 U | 12/2021 |
| CN | 114089024 A | 2/2022 |
| JP | 2001324519 A | 11/2001 |
| SU | 1628021 A | 2/1991 |

OTHER PUBLICATIONS

Office Action dated Mar. 3, 2022 issued for Chinese Patent Application No. 202210063946.7.

International Search Report dated Feb. 24, 2023 issued for Internatioanl PCT Application No. PCT/CN2022/136564.

Shen Bin, Professor Wang Huifeng, Associate Professor Ji Jianhua, "Research of the Preamplifier Using in the Nanopore DNA Sequencing", Master's degree in East China University of Science and Technology, Dec. 17, 2013, China Academic Journal Electronic Publishing House, http://www.cnki.net.

Brian Goldstein, et al., "CMOS Low Current Measurement System for Biomedical Applications",, IEEE Transactions On Biomedical Circuits and Systems, vol. 6, No. 2, Apr. 2012.

* cited by examiner

CURRENT MEASUREMENT CIRCUIT, CURRENT MEASUREMENT METHOD AND NANOPORE SEQUENCING DEVICE

CROSS-REFERENCE TO RELATED APPLICATION

This application is a continuation of International Application No. PCT/CN2022/136564, filed on Dec. 5, 2022, which claims priority to Chinese Patent Application No. 202210063946.7, entitled "CURRENT MEASUREMENT CIRCUIT, CURRENT MEASUREMENT METHOD AND NANOPORE SEQUENCING DEVICE", filed on Jan. 20, 2022, both of which are hereby incorporated by reference in their entireties.

TECHNICAL FIELD

The present application relates to the technical field of nanopore sequencing, and in particular, to a current measurement circuit, a current measurement method and a nanopore sequencing device.

BACKGROUND

Nanopore gene sequencing is to determine a gene sequence passing through a thin film nanopore by measuring a current signal flowing through the thin film nanopore. When measuring the current, since the current value is very small (usually tens to hundreds of picoamperes, sometimes up to thousands of picoamperes), it is necessary to use an amplifier circuit for measurement, usually using a capacitive trans impedance amplifier (CTIA) circuit for measurement.

The capacitive trans impedance amplifier circuit converts the current signal into a voltage signal during measurement and amplifies the voltage signal. An analog to digital conversion unit (ADC) is used to sample the amplified voltage signal to obtain a measurement result. In the above method, the capacitive trans impedance amplifier circuit has infinite gain, and a capacitor needs to be discharged periodically. During the periodical discharge operation, an instantaneous current formed by the discharging may interfere with an adjacent extremely weak measured current signal, which affects a final accuracy of current measurement.

SUMMARY

Embodiments of the present application provide a current measurement circuit, a current measurement method and a nanopore sequencing device.

In a first aspect, the embodiments of the present application provide a current measurement circuit, including: an amplification unit, electrically connected to a sensor unit and configured to amplify an electrical signal from the sensor unit; a comparison unit, electrically connected to the amplification unit and configured to: output a high level under a condition that a voltage signal output by the amplification unit is greater than a preset voltage, and output a low level under a condition that the voltage signal output by the amplification unit is less than the preset voltage, to obtain an initial pulse signal; a delay unit, electrically connected to the comparison unit and configured to delay an output of the initial pulse signal to obtain a target pulse signal; a resistance unit, wherein two terminals of the resistance unit are electrically connected to an input terminal of the amplification unit and an output terminal of the delay unit respectively, and the resistance unit is configured to feed back charging and discharging currents to the amplification unit based on the target pulse signal; and a calculation unit, electrically connected to the delay unit and configured to calculate a target current based on the target pulse signal output by the delay unit, wherein the target current is a current flowing through the sensor unit.

In a second aspect, the embodiments of the present application provide a current measurement method realized by the current measurement circuit of the first aspect, including: amplifying, by the amplification unit, the electrical signal from the sensor unit; outputting, by the comparison unit, the high level under a condition that the voltage signal output by the amplification unit is greater than the preset voltage and the low level under a condition that the voltage signal output by the amplification unit is less than the preset voltage, to obtain the initial pulse signal; delaying, by the delay unit, the output of the initial pulse signal to obtain the target pulse signal; feeding back, by the resistance unit, the charging and discharging currents to the amplification unit based on the target pulse signal; and calculating, by the calculation unit, the target current based on the target pulse signal output by the delay unit, wherein the target current is the current flowing through the sensor unit.

In a third aspect, the embodiments of the present application provide a nanopore sequencing device, including the current measurement circuit of the first aspect.

BRIEF DESCRIPTION OF THE DRAWINGS

In order to more clearly illustrate technical solutions of the embodiments of the present application, the accompanying drawings that need to be used in the embodiments of the present application will be briefly introduced below. For those skilled in the art, additional drawings can be derived from these accompanying drawings without any inventive effort.

DETAILED DESCRIPTION

Features and exemplary embodiments of various aspects of the present application will be described in detail below, and in order to make objects, technical solutions and advantages of the present application more clear and apparent, the present application is further described in detail below in conjunction with the drawings and specific embodiments. It should be understood that specific embodiments described herein are only intended to interpret the present application, and are not intended to limit the present application. For those skilled in the art, the present application may be practiced without some of these specific details. The following description of the embodiments is only intended to provide a better understanding of the present application by illustrating examples of the present application.

It should be noted that, relational terms herein such as "first" and "second", and the like, are only used to distinguish one entity or operation from another entity or operation, and do not necessarily require or imply any such actual relationship or order between these entities or operations. Furthermore, terms "comprising", "including", or any other variant thereof, are intended to cover a non-exclusive inclusion, such that a process, method, article, or apparatus including a series of elements includes not only those elements, but also other elements not expressly listed or elements inherent to such process, method, article, or apparatus. Without further restrictions, an element qualified by "includes . . . " does not exclude an existence of additional identical elements in the process, method, article, or apparatus that includes the element.

Currently, under a condition that a capacitive trans impedance amplifier (CTIA) circuit is used for weak current measurement, since the capacitive trans impedance amplifier circuit has infinite gain, a capacitor needs to be discharged periodically, which increases the complexity of the circuit. At the same time, an instantaneous current generated by the discharging will also affect the adjacent extremely weak measured current, which affects an accuracy of the measurement.

In order to solve problems in the prior art, the embodiments of the present application provide a current measurement circuit, a current measurement method, and a nanopore sequencing device. The current measurement circuit according to the embodiments of the present application will be firstly introduced below.

Figure 1:
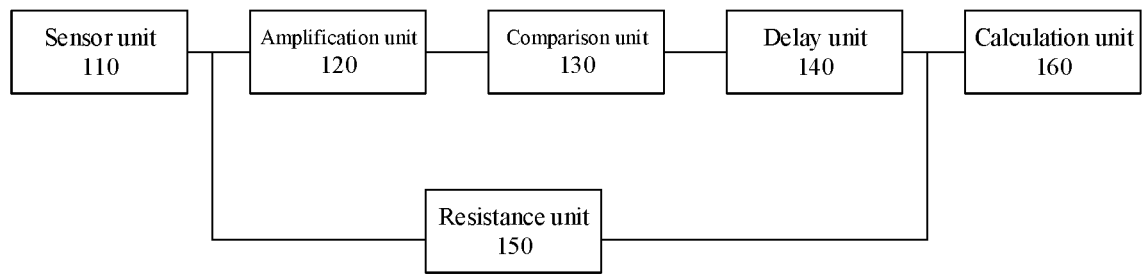
FIG. 1 is a schematic structural diagram of a current measurement circuit according to an embodiment of the present application.

FIG. 1 illustrates a schematic structural diagram of a current measurement circuit according to an embodiment of the present application. As shown in FIG. 1, the current measurement circuit includes: an amplification unit 120, electrically connected to a sensor unit 110 and configured to amplify an electrical signal from the sensor unit 110; a comparison unit 130, electrically connected to the amplification unit 120 and configured to: output a high level under a condition that a voltage signal output by the amplification unit 120 is greater than a preset voltage, and output a low level under a condition that the voltage signal output by the amplification unit 120 is less than the preset voltage, to obtain an initial pulse signal; a delay unit 140, electrically connected to the comparison unit 130 and configured to delay an output of the initial pulse signal to obtain a target pulse signal; a resistance unit 150, wherein two terminals of the resistance unit 150 are electrically connected to an input terminal of the amplification unit 120 and an output terminal of the delay unit 140 respectively, and the resistance unit 150 is configured to feed back charging and discharging currents to the amplification unit 120 based on the target pulse signal; and a calculation unit 160, electrically connected to the delay unit 140 and configured to calculate a target current based on the target pulse signal output by the delay unit, wherein the target current is a current flowing through the sensor unit 110.

In the embodiments of the present application, an equivalent resistance and a parasitic equivalent parallel capacitance of a thin film nanopore included in the sensor unit 110 are connected in parallel, one terminal of the sensor unit 110 is connected to the ground, and the other terminal of the sensor unit 110 is connected to the amplification unit 120. The target current is output to the subsequent amplification unit 120 through the equivalent resistance and parasitic equivalent parallel capacitance of the thin film nanopore.

In the embodiments of the present application, the input terminal of the amplification unit 120 is electrically connected to the equivalent resistance and parasitic equivalent parallel capacitance of the thin film nanopore, and the amplification unit 120 may be configured to amplify the electrical signal of an electrical connection point between the amplification unit 120 and the sensor unit 110 via the target current, so as to output the amplified signal to the subsequent comparison unit 130, wherein the amplification unit is an integral amplification circuit.

In the embodiments of the present application, an input terminal of the comparison unit 130 is electrically connected to an output terminal of the amplification unit 120, and the comparison unit 130 is configured to: output the high level under a condition that the voltage signal output by the amplification unit 120 is greater than the preset voltage, and output the low level under a condition that the voltage signal output by the amplification unit 120 is less than the preset voltage, to obtain the initial pulse signal for output to the subsequent delay unit 140.

In the embodiments of the present application, an input terminal of the delay unit 140 is electrically connected to the output terminal of the comparison unit 130, and the delay unit 140 may be configured to delay the output of the initial pulse signal output by the comparison unit 130, to obtain the target pulse signal for output to the subsequent computing unit 160.

In the embodiments of the present application, the two terminals of the resistance unit 150 are electrically connected to the input terminal of the amplification unit 120 and the output terminal of the delay unit 140 respectively. Under a condition that the target pulse signal output by the delay unit 140 is at a high level, a current direction of a loop where the resistance unit 150 is located is from the output terminal of the delay unit 140 to the input terminal of the amplification unit 120 (see a direction indicated by an arrow I1 in FIG. 2). Under a condition that the target pulse signal output by the delay unit 140 is at a low level, the current direction of the loop where the resistance unit 150 is located is from the input terminal of the amplification unit 120 to the output terminal of the delay unit 140 (see a direction indicated by an arrow I2 in FIG. 2).

In the embodiments of the present application, an input terminal of the calculation unit 160 is electrically connected to the output terminal of the delay unit 140, and the calculation unit 160 is configured to calculate a value of the target current based on a pulse voltage generated by the target pulse signal output by the delay unit 140.

In the embodiments of the present application, one terminal of the equivalent resistance and parasitic equivalent parallel capacitance of the thin film nanopore is connected to the ground, the amplification unit amplifies the electrical signal across the equivalent resistance and parasitic equivalent parallel capacitance of the thin film nanopore via the target current, and the amplified voltage signal is output through the comparison unit and the delay unit to obtain the target pulse signal. Under a condition that the output voltage signal is a high level of the pulse signal, discharging may be performed through the loop where the resistance unit is located. The value of the target current is calculated based on the voltage pulse signal, which avoids an influence of instantaneous current generated when the capacitor is discharged periodically, thereby improving an accuracy of current measurement.

Figure 2:
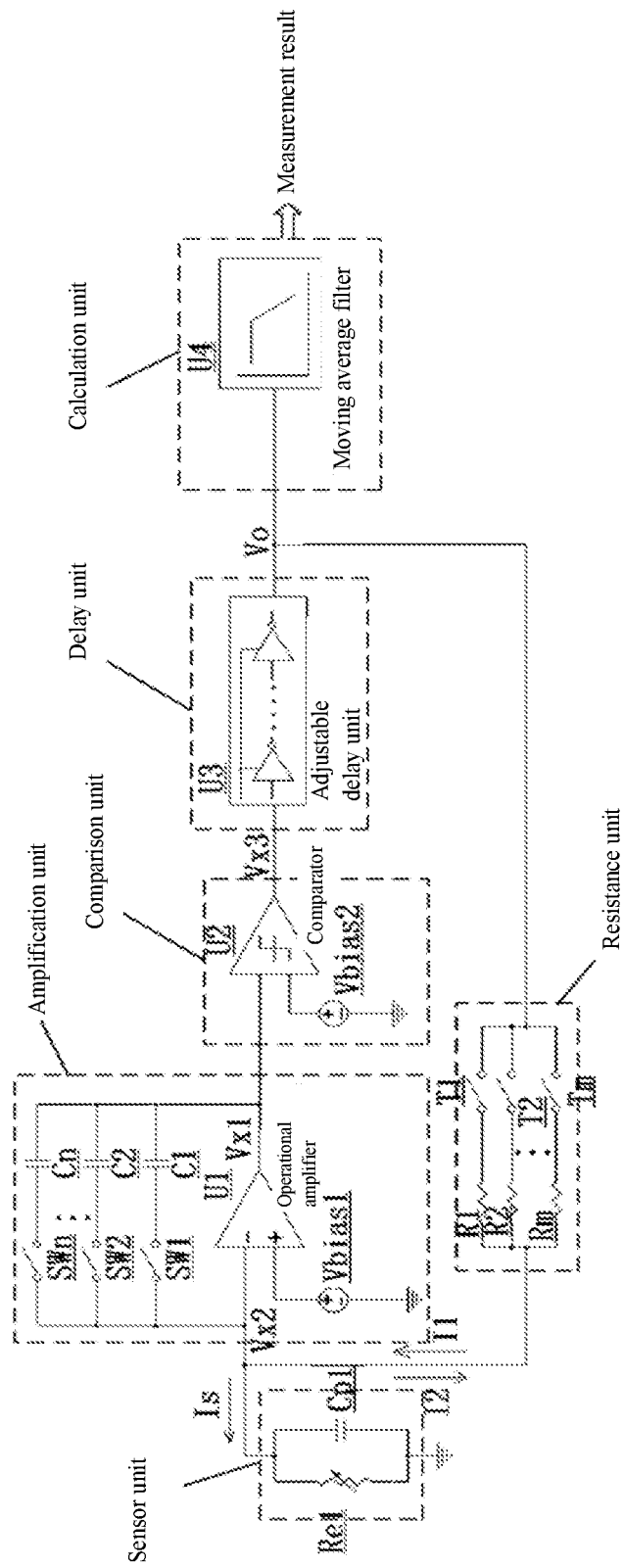
FIG. 2 is a schematic diagram of a current measurement circuit according to an embodiment of the present application.

FIG. 2 illustrates a schematic structural diagram of a current measurement circuit according to a specific embodiment of the present application. As shown in FIG. 2, the amplification unit includes an operational amplifier U1 and an integrating capacitor, wherein a non-inverting input terminal of the operational amplifier is configured to access an operating voltage Vbias1, an inverting input terminal of the operational amplifier is electrically connected to the sensor unit, and an output terminal of the operational amplifier is electrically connected to one terminal of the integrating capacitor and to the comparison unit, and the other terminal of the integrating capacitor is electrically connected to the inverting input terminal of the operational amplifier. The operating voltage Vbias1 accessed by the operational amplifier is an operating voltage of nanopore sequencing.

In some embodiments, the integrating capacitor includes n capacitors connected in parallel, and the amplification unit further includes n first switches, each of the first switches is connected in series with a capacitor, wherein n is an integer greater than or equal to 2, capacitance values of the n capacitors are different.

As shown in FIG. 2, the integrating capacitor connected to the operational amplifier includes a plurality of parallel capacitors C1, C2, . . . , Cn, and each of the parallel capacitors is connected in series with one of the first switches SW1, SW2, . . . , SWn.

In some embodiments, as shown in FIG. 2, the sensor unit includes a thin film nanopore equivalent resistance Re1 and a thin film nanopore parasitic equivalent parallel capacitance Cp1 connected in parallel. One terminal of the sensor unit is connected to the ground, and the other terminal of the sensor unit is electrically connected to the inverting input terminal of the operational amplifier U1. The sensor unit is configured to generate a target current Is. Since one terminal of the sensor unit is connected to the ground and a voltage of the terminal is 0, and the other terminal of the sensor unit is connected to the inverting input terminal of the operational amplifier U1 and under a condition that the operational amplifier U1 is in a linear operating area, a voltage Vx2 of the inverting input terminal is equal to a voltage of the non-inverting input terminal, and both the voltages are Vbias1, therefore the target current Is flowing through the thin film nanopore equivalent resistance Re1 and the thin film nanopore parasitic equivalent parallel capacitance Cp1 is generated.

Specifically, the present application is applied to a nanopore gene sequencing device. In the device, an insulating thin film with a nanoscale pore divides a liquid chamber into two small chambers, each of the two small chambers has an electrode, and two electrodes have different potentials. Driven by an electrode potential difference, single-stranded DNA (ssDNA) passes from one chamber through the nanoscale hole on the insulating thin film to another chamber. When single-stranded DNA passes through the nanopore, due to a difference in properties of different bases, a current between the electrodes will change in amplitude. By reading the change in the current between the electrodes, DNA sequence information can be obtained. In FIG. 2, Re1 is the equivalent resistance of the thin film nanopore, and Cp1 is the parasitic equivalent parallel capacitance of the thin film nanopore. When single-stranded DNA passes through the nanopore, due to a blockage by the bases to the thin film nanopore, a resistance of the thin film nanopore to the current between the electrodes becomes larger, and due to the difference in properties of different bases, degrees of blockage to the thin film nanopore by different bases are different, therefore the thin film nanopore in FIG. 2 is equivalent to a variable resistor Re1; that is, a resistance value of Re1 in FIG. 2 changes, then the current Is to be measured flowing through the thin film nanopore changes. When performing gene sequencing, a magnitude of Is is between tens and hundreds of picoamperes. The present application is used to measure the current signal Is during gene sequencing. Under a condition that the operational amplifier U1 is in the linear operating area, the voltage Vx2 of the inverting input terminal of the operational amplifier U1 is equal to a voltage of the non-inverting input terminal of the operational amplifier U1, and both the voltages are Vbias1. Vbias1 is the potential difference between the electrodes in the two small chambers when performing nanopore gene sequencing, namely, the operating voltage of nanopore sequencing.

In some embodiments, the comparison unit includes a voltage comparator, an inverting input terminal of the voltage comparator is configured to access the preset voltage; a non-inverting input terminal of the voltage comparator is electrically connected to an output terminal of the amplification unit, and the voltage comparator is configured to: output the high level under a condition that the voltage signal received from the amplification unit is greater than the preset voltage, and output the low level under a condition that the voltage signal received from the amplification unit is less than the preset voltage, to obtain the initial pulse signal; an output terminal of the voltage comparator is electrically connected to an adjustable delay unit. As shown in FIG. 2, the voltage comparator U2 is connected to a threshold voltage Vbias2, and compares a voltage Vx1 output by the amplification unit with the threshold voltage Vbias2. Under a condition that Vx1 is greater than Vbias2, a high level VH is output; under a condition that Vx1 is less than Vbias2, a low level VL is output, that is, the voltage comparator U2 outputs an initial voltage pulse signal Vx3 whose high level is VH and low level is VL (see FIG. 3). It should be known that, a value of the preset voltage, high level, and low level can be set, the embodiments of the present application does not limit the value of the preset voltage, high level, and low level, but the high level of the voltage comparator should be higher than the operating voltage and the low level of the voltage comparator should be lower than the operating voltage.

In some embodiments, the delay unit includes the adjustable delay unit, an input terminal of the adjustable delay unit is electrically connected to the output terminal of the voltage comparator; an output terminal of the adjustable delay unit is electrically connected to the calculation unit, the adjustable delay unit is configured to delay the output of the initial pulse signal to obtain the target pulse signal. As shown in FIG. 2, the adjustable delay unit may be formed by cascading multiple voltage-controlled delay inverters. The adjustable delay unit U3 delays and outputs the obtained initial voltage pulse signal Vx3 based on a preset time delay Td to obtain the target pulse signal Vo.

In some embodiments, the resistance unit includes m resistors connected in parallel, where m is an integer greater than or equal to 2, and resistance values of the m resistors are different. Under a condition that an output voltage of the delay unit is at a high level, since the high level is higher than the operating voltage of the electrical connection point between the amplification unit and the sensor unit, a current flowing from the output terminal of the delay unit, through the resistance unit, to the input terminal of the amplification unit is generated, thereby providing a discharging current to the integrating capacitor of the amplification unit; under a condition that the output voltage of the delay unit is at a low level, since the low level is lower than the operating voltage of the electrical connection point between the amplification unit and the sensor unit, a current flowing from the input terminal of the amplification unit, through the resistance unit, to the output terminal of the delay unit is generated, thereby providing a charging current to the integrating capacitor of the amplification unit. Current values of the charging current and the discharging current may be calculated through the output voltage of the delay unit and a resistor. Specifically, a ratio of the output voltage of the delay unit to a resistor in the resistance unit is a current of a loop where the resistor is located. Under a condition that the integrating capacitor is discharged, a direction of the current of the loop is a direction shown by I1 in FIG. 2, a magnitude I1 of the current of the loop is (VH-Vbias1)/Rn, Rn is any resistor selected from R1-Rm, and a magnitude of the discharging current provided to the integrating capacitor of the amplification unit is I1−Is; under a condition that the integrating capacitor is charged, the direction of the current of the loop is a direction shown by I2 in FIG. 2, a magnitude I2 of the current of the loop is (Vbias1-VL)/Rn, Rn is any resistor selected from R1-Rm, and a magnitude of the charging current provided to the integrating capacitor of the amplification unit is I2+Is.

In some embodiments, the resistance unit further includes m second switches, and each of the second switches is connected in series with a resistor.

As shown in FIG. 2, the resistance unit includes m resistors R1, R2, . . . , Rm connected in parallel, and each of the resistors is connected in series with a switch T1, T2, . . . , Tm.

In some embodiments, the calculation unit is electrically connected to the delay unit and is configured to calculate the target current based on the target pulse signal output by the delay unit, wherein the target current is the current flowing through the sensor unit. Calculating the target current based on the target pulse signal output by the delay unit includes: calculating, by the calculation unit, the target current based on a frequency and a duty cycle of the target pulse signal output by the delay unit; or performing, by the calculation unit, moving average calculation based on the target pulse signal output by the delay unit to obtain a value of the target current. When calculating the target current, a charging or discharging speed of the integrating capacitor is much faster than a changing speed of the target current signal Is, that is, the target current signal Is remains relatively constant during one charging and discharging cycle of the integrating capacitor. Under a condition that the calculation unit calculates the target current based on the duty cycle of the target voltage pulse signal output by the delay unit, a length of time $T_H$ for Vo to output a high level VH, and a length of time $T_L$ for Vo to output a low level VL during one charging and discharging cycle of the integrating capacitor is calculated based on the preset time delay Td of the delay unit:

$$T_H = \frac{I1 + I2}{I1 - Is} Td$$

$$T_L = \frac{I1 + I2}{I2 + Is} Td$$

wherein, I1 is a current of a loop where the resistance unit is located when the integrating capacitor is discharged, and I2 is a current of the loop where the resistance unit is located when the integrating capacitor is charged.

Based on the duty cycle D of the high level VH of the target pulse signal Vo being $$D = \frac{T_H}{T_H + T_L},$$

the target current Is is calculated as:

$$Is = DI1 + (D-1)I2$$

Under a condition that the calculation unit is configured for performing moving average calculation based on the voltage pulse signal output by the delay unit, an average value of output voltages within a period of time window is obtained through calculation, and the target current is calculated based on the charging current value and the discharging current value.

In some embodiments, the frequency and the duty cycle of the target pulse signal vary with a change of the target current.

In some embodiments, varying of the frequency and duty cycle of the target pulse signal with a change of the target current includes: under a condition that the target current increases, an output waveform of the target pulse signal varies in a manner that: a low-level duty cycle becomes larger, and a high-level duty cycle becomes smaller.

In some embodiments, varying of the frequency and duty cycle of the target pulse signal with a change of the target current further includes: under a condition that the target current decreases, the output waveform of the target pulse signal varies in a manner that: the low-level duty cycle becomes smaller, and the high-level duty cycle becomes larger.

In some embodiments, the computing unit includes a Field Programmable Gate Array (FPGA), or a Micro Control Unit (MCU). A process of calculating the target current based on the frequency and duty cycle of the voltage pulse signal output by the delay unit, or performing moving average calculation based on the voltage pulse signal output by the delay unit to obtain the value of the target current may be realized by the FPGA or MCU.

In some embodiments, the sensor unit includes the equivalent resistance and the parasitic equivalent parallel capacitance of the thin film nanopore.

In some embodiments, the target current is the current flowing through the thin film nanopore during nanopore gene sequencing.

As shown in FIG. 2, the calculation unit includes a moving average filter U4. It should be known that, the moving average filter U4 may be replaced by other computing devices, and FIG. 2 is only an example.

For the circuit diagram as shown in FIG. 2, its operating principle is as follows: during a current measurement, the non-inverting input terminal of the operational amplifier U1 is connected to the operating voltage Vbias1, the charging and discharging currents input to the integrating capacitor connected to the inverting input terminal of the operational amplifier is obtained based on the target current Is generated by the sensor unit and a current flowing through the resistance unit I1/I2, wherein a voltage at the electrical connection point Vx2 of the inverting input is Vbias1. After the charging and discharging currents is transmitted to the integrating capacitor, the integrating capacitor integrates the two current signals to obtain a voltage signal Vx1, and the output terminal of the operational amplifier transmits the voltage signal Vx1 to the comparison unit. The voltage comparator U2 of the comparison unit compares the received voltage signal Vx1 with the threshold voltage Vbias2, and outputs the initial pulse signal Vx3 to the input terminal of the adjustable delay unit U3. The adjustable delay unit U3 outputs the target pulse signal Vo to the calculation unit U4 after the received initial pulse signal Vx3 is delayed by the preset time delay Td. Based on a voltage difference between the target pulse signal Vo and the voltage Vbias1 of the inverting input terminal of the operational amplifier U1, a corresponding current I1 or I2 passing through the resistance unit is generated. At the same time, the calculation unit U4 calculates the target current Is based on the voltage pulse signal Vo. Under a condition that the target pulse signal Vo is greater than the voltage Vbias1 of the inverting input terminal Vx2 of the operational amplifier U1, a current I1 flowing from the output terminal of the delay unit, through the resistance unit, to the input terminal of the amplification unit is generated; under a condition that the target pulse signal Vo is lower than the voltage Vbias1 of the inverting input terminal Vx2 of the operational amplifier U1, a current I2 flowing from the input terminal of the amplification unit, through the resistance unit, to the output terminal of the delay unit is generated.

Specifically, for n integrating capacitors connected in parallel, it is necessary to select a switch corresponding to one of the capacitors to be turned on, and the remaining switches are in a turn-off state. Under a condition that the measured target current Is is relatively large, an integrating capacitor with a relatively large capacitance value is selected to acquire a larger measurement range; under a condition that the measured target current Is is relatively small, an integrating capacitor with a relatively small capacitance value is selected to acquire a smaller measuring range. For m resistors connected in parallel, it is necessary to select a switch corresponding to one of the resistors to be turned on, and the remaining switches are all in a turn-off state. Under a condition that the measured target current Is is relatively large, a resistor with a relatively small resistance value is selected to provide relatively large charging and discharging currents I1, I2; under a condition that the measured target current Is is relatively small, a resistor with a relatively large resistance value is selected to provide relatively small charging and discharging currents I1, I2. For the time delay Td of the adjustable delay unit, under a condition that the target current Is is relatively small, the preset time delay may be increased; under a condition that the target current I s is relatively large, the preset time delay may be decreased. Based on a selection of the integrating capacitor, resistor, and time delay, it can be ensured that, under a condition that the nanopore sequencing current Is changes in a large range, the frequency and duty cycle of the output pulse width modulation signal Vo remain within a certain reasonable range, and a current measurement range of a current measurement circuit can be adjusted. Under a condition that the calculation unit uses a method of moving average for calculation, a moving time window Ta can also be adjusted to adjust an accuracy of a current measurement result.

Figure 3:
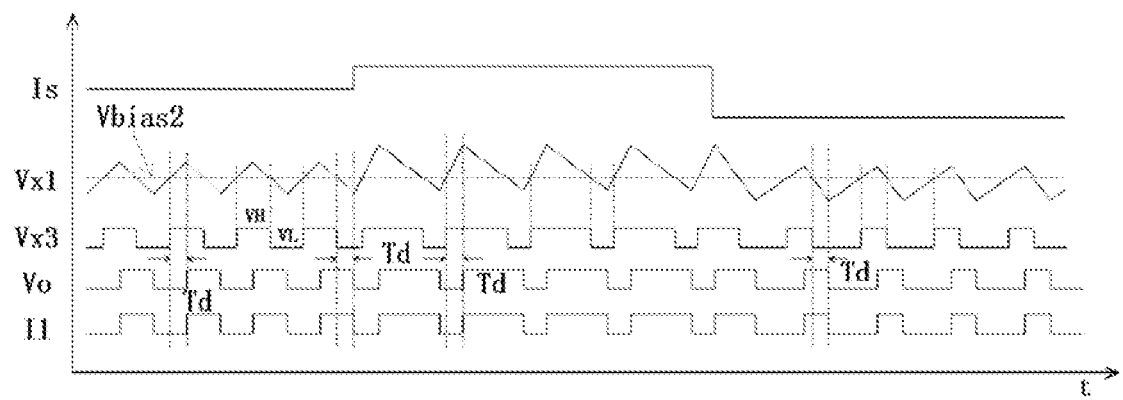
FIG. 3 is a timing waveform diagram of voltages and currents of various nodes according to an embodiment of the present application.

In one embodiment, timing waveforms of voltages and currents of various nodes are shown in FIG. 3. In conjunction with FIG. 2 and FIG. 3, under a condition that the pulse signal Vo is at the low level VL, the adjustable delay unit U3 charges the integrating capacitor through the charging current I2, and the output voltage Vx1 of the amplification unit gradually increases.

Under a condition that the voltage Vx1 output by the amplification unit increases to be higher than the threshold voltage Vbias2 of the voltage comparator, the output of the voltage comparator U2 is reversed, and the output voltage pulse signal Vx3 jumps from the low level VL to the high level VH.

After a delay of certain time period (Td), the output voltage pulse signal Vo of the adjustable delay unit U3 is reversed, and jumps from the low level VL to the high level VH.

The adjustable delay unit U3 starts to discharge the integrating capacitor through the discharging current I1 (I1>Is, which is a prerequisite for normal operation of a pulse width modulation current measurement circuit, that is, the nanopore sequencing current Is must be less than the discharging current I1), and the voltage Vx1 output by the amplification unit gradually decreases.

Under a condition that the voltage Vx1 output by the amplification unit drops below the threshold voltage Vbias2 of the voltage comparator, the voltage comparator U2 is reversed, and its output voltage pulse signal Vx3 jumps from the high level VH to the low level VL.

After a delay of certain time period (Td), the output voltage pulse signal Vo of the adjustable delay unit U3 jumps from the high level VH to the low level VL.

Under a condition that the target current Is increases, the charging current I2+Is of the integrating capacitor increases, a charging rate of the integrating capacitor accelerates, and a rising slope of Vx1 becomes larger; at the same time, the discharging current I1−Is of the integrating capacitor decreases, and a discharging rate of the integrating capacitor slows down, and a falling slope of Vx1 becomes smaller. The output waveform of the pulse signal Vo varies in a manner that: the low-level VL duty cycle becomes smaller, and the high-level VH duty cycle becomes larger.

Under a condition that the target current Is decreases, the charging current I2+Is of the integrating capacitor decreases, the charging rate of the integrating capacitor slows down, and the rising slope of Vx1 decreases; at the same time, the discharging current I1−Is of the integrating capacitor increases, and the discharging rate of the integrating capacitor becomes faster, and the falling slope of Vx1 becomes larger. The output waveform of the pulse signal Vo varies in a manner that: the low-level VL duty cycle becomes larger, and the high-level VH duty cycle becomes smaller.

It can be known from the above contents that, the pulse signal Vo is a pulse width modulation signal, and a change of its duty cycle can reflect a change of the target current Is as an analog signal.

Both I1 and I2 are of known current magnitudes, where I1 is the current of the loop where the resistance unit is located when the integrating capacitor is discharged, and I2 is the current of the loop where the resistance unit is located when the integrating capacitor is charged. By calculating the pulse width modulation signal Vo, the nanopore sequencing current Is may be calculated. Specifically, when the calculation unit calculates the target current based on the duty cycle of Vo, the length of time $T_H$ for Vo to output the high level VH, and the length of time $T_L$ for Vo to output the low level VL during one charging and discharging cycle of the integrating capacitor is calculated based on the time delay Td.

Based on the duty cycle D of the high level VH of the target pulse signal Vo, the target current Is is calculated.

In the embodiments of the present application, a current integrating circuit can be combined to amplify a weak current flowing through the thin film nanopore and convert it into a pulse width modulation signal, and a measurement result of the current signal is obtained by measuring the frequency and duty cycle of the pulse width modulation signal, or by performing moving average calculation on the pulse width modulation signal, which has characteristics of high gain and high linearity. At the same time, a problem of noise interference brought by the periodical discharging of the capacitor to an adjacent nanopore sequencing channel is solved, which increases a current measurement range.

Figure 4:
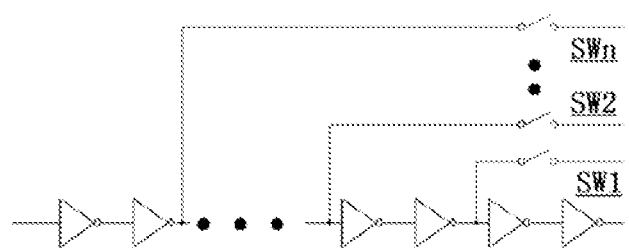
FIG. 4 is a schematic structural diagram of an adjustable delay unit according to an embodiment of the present application.
Figure 5:
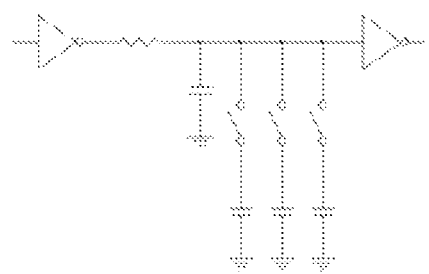
FIG. 5 is a schematic structural diagram of another adjustable delay unit according to an embodiment of the present application.

In some embodiments, the adjustable delay unit may be realized by cascading different numbers of delay inverters, as shown in FIG. 4. Alternatively, the adjustable delay unit is realized by setting different delay capacitance values, as shown in FIG. 5. Alternatively, the adjustable delay unit is realized by FPGA.

In some embodiments, measurement of the frequency and duty cycle of the voltage pulse signal output by the delay unit may be realized by a circuit such as a counter.

Figure 6:
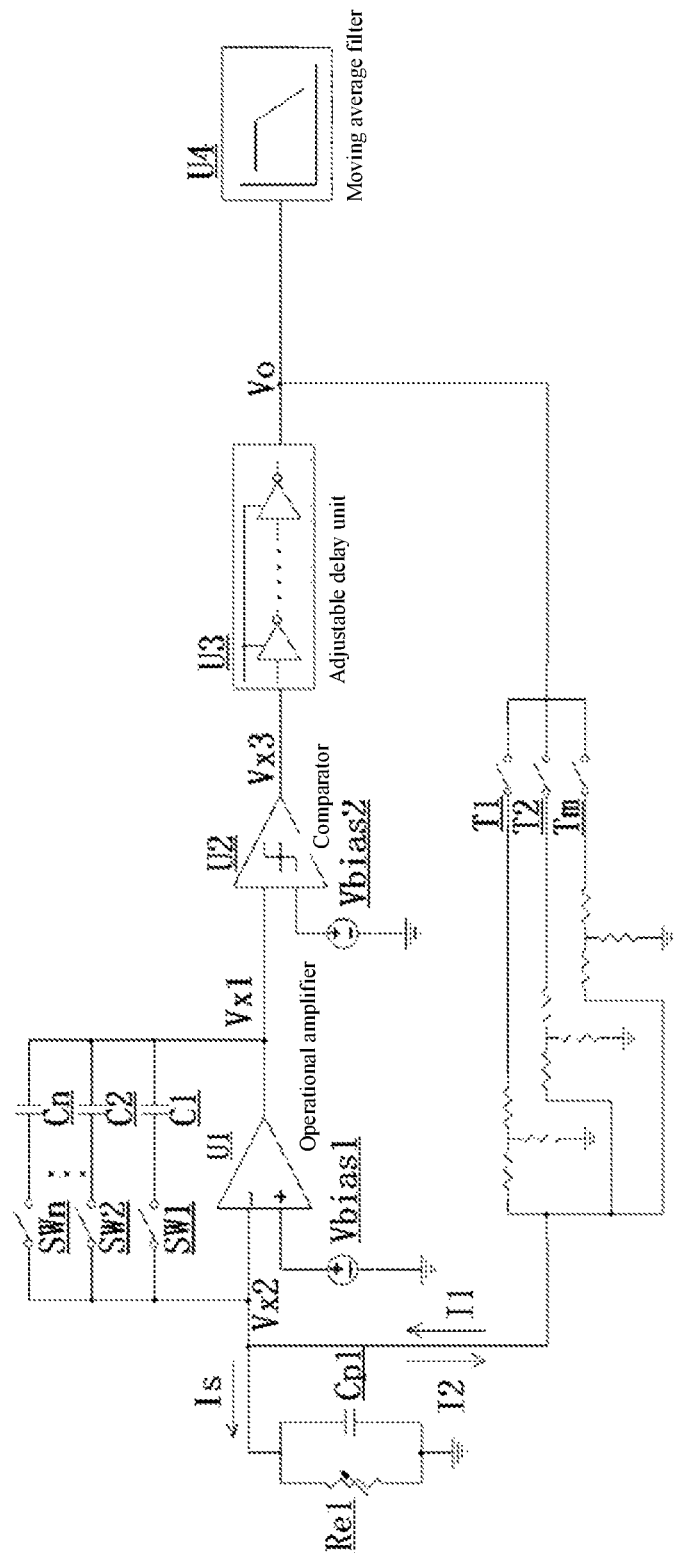
FIG. 6 is a schematic structural diagram of a resistance unit according to an embodiment of the present application.

In some embodiments, as shown in FIG. 6, the resistance unit may be realized by using a T-shaped resistance network, which can reduce an area occupied by the resistance unit in an integrated circuit.

Figure 7:
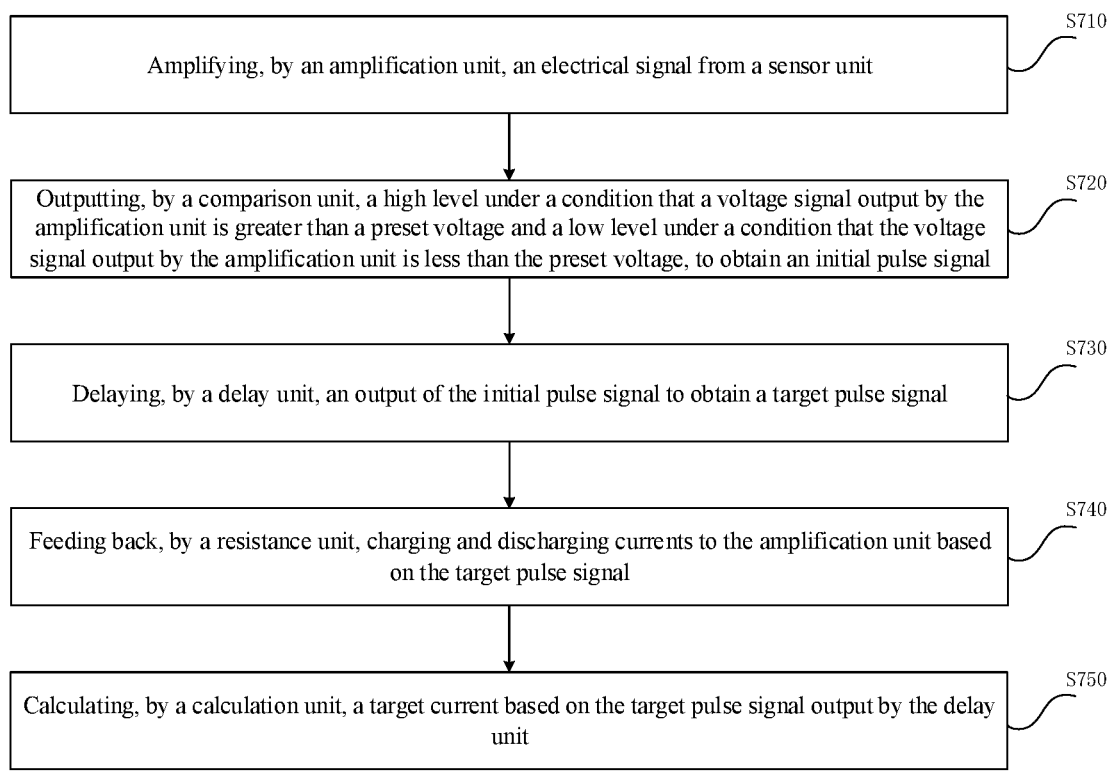
FIG. 7 is a schematic flow chart of a current measurement method according to an embodiment of the present application.

FIG. 7 illustrates a schematic flowchart of a current measurement method according to an embodiment of the present application. The current measurement method of the present application may be implemented by the above-mentioned current measurement circuit, and the method includes steps 710 to 750.

At step 710, the electrical signal from the sensor unit is amplified by the amplification unit.

At step 720, the high level is output by the comparison unit under a condition that the voltage signal output by the amplification unit is greater than the preset voltage and the low level is output by the comparison unit under a condition that the voltage signal output by the amplification unit is less than the preset voltage, to obtain the initial pulse signal.

At step 730, the output of the initial pulse signal is delayed by the delay unit to obtain the target pulse signal.

At step 740, the charging and discharging currents are fed back by the resistance unit to the amplification unit based on the target pulse signal.

At step 750, the target current is calculated by the calculation unit based on the target pulse signal output by the delay unit, wherein the target current is the current flowing through the sensor unit.

It should be noted that, all relevant contents of various steps involved in the above-mentioned method embodiments may be implemented based on corresponding functional units, and can achieve corresponding technical effects. For the sake of brevity, details will not be repeated herein.

Based on the current measurement circuit in the above embodiments, the present application also provides a nanopore sequencing device including a current measurement circuit, and the device may be configured to measure the target current.

The above contents are only specific implementations of the present application, and those skilled in the art can clearly understand that for the convenience and brevity of description, the specific operating process of the above-described systems, modules and units may refer to the above-mentioned method embodiments, which will not be repeated herein. It should be understood that a protection scope of the present application is not limited thereto, any person skilled in the art can easily think of various equivalent modifications or replacements within a technical scope disclosed in the present application, and these modifications or replacements shall be covered within the protection scope of the present application.

What is claimed is:

1. A current measurement circuit, comprising:
an amplification unit, electrically connected to a sensor unit and configured to amplify an electrical signal from the sensor unit;
a comparison unit, electrically connected to the amplification unit and configured to: output a high level under a condition that a voltage signal output by the amplification unit is greater than a preset voltage, and output a low level under a condition that the voltage signal output by the amplification unit is less than the preset voltage, to obtain an initial pulse signal;
a delay unit, electrically connected to the comparison unit and configured to delay an output of the initial pulse signal to obtain a target pulse signal;
a resistance unit, wherein two terminals of the resistance unit are electrically connected to an input terminal of the amplification unit and an output terminal of the delay unit respectively, and the resistance unit is configured to feed back charging and discharging currents to the amplification unit based on the target pulse signal; and
a calculation unit, electrically connected to the delay unit and configured to calculate a target current based on the target pulse signal output by the delay unit, wherein the target current is a current flowing through the sensor unit,
wherein the calculation unit is configured to calculate the target current based on the target pulse signal output by the delay unit by:
calculating the target current based on a frequency and a duty cycle of the target pulse signal output by the delay unit; or
performing moving average calculation based on the target pulse signal output by the delay unit to obtain a value of the target current.

2. The current measurement circuit of claim 1, wherein the amplification unit comprises an operational amplifier and an integrating capacitor;
a non-inverting input terminal of the operational amplifier is configured to access an operating voltage;
an inverting input terminal of the operational amplifier is electrically connected to the sensor unit, and an output terminal of the operational amplifier is electrically connected to one terminal of the integrating capacitor and to the comparison unit, and the other terminal of the integrating capacitor is electrically connected to the inverting input terminal of the operational amplifier.

3. The current measurement circuit of claim 2, wherein the integrating capacitor comprises n capacitors connected in parallel, the amplification unit further comprises n first switches, each of the first switches is connected in series with a capacitor, wherein n is an integer greater than or equal to 2, capacitance values of the n capacitors are different, and one of the n capacitors is selectable as the integrating capacitor based on a magnitude of the target current.

4. The current measurement circuit of claim 1, wherein the comparison unit comprises a voltage comparator;
an inverting input terminal of the voltage comparator is configured to access the preset voltage;
a non-inverting input terminal of the voltage comparator is electrically connected to an output terminal of the amplification unit, and the voltage comparator is configured to: output a high level under a condition that the voltage signal output by the amplification unit is greater than the preset voltage, and output a low level under a condition that the voltage signal output by the amplification unit is less than the preset voltage, to obtain the initial pulse signal;

an output terminal of the voltage comparator is electrically connected to the delay unit.

5. The current measurement circuit of claim 1, wherein the delay unit comprises an adjustable delay unit;

an input terminal of the adjustable delay unit is electrically connected to an output terminal of the voltage comparator;

an output terminal of the adjustable delay unit is electrically connected to the calculation unit;

an output delay of the adjustable delay unit is adjustable based on a magnitude of the target current.

6. The current measurement circuit of claim 1, wherein the resistance unit comprises m resistors connected in parallel, wherein m is an integer greater than or equal to 2, resistance values of the m resistors are different, and one of the m resistors is selectable as the resistance unit based on a magnitude of the target current.

7. The current measurement circuit of claim 6, wherein the resistance unit further comprises m second switches, and each of the second switches is connected in series with a resistor.

8. The current measurement circuit of claim 1, wherein the frequency and the duty cycle of the target pulse signal vary with a change of the target current.

9. The current measurement circuit of claim 8, wherein varying of the frequency and duty cycle of the target pulse signal with a change of the target current comprises:

under a condition that the target current increases, an output waveform of the target pulse signal varies in a manner that: a low-level duty cycle becomes larger, and a high-level duty cycle becomes smaller.

10. The current measurement circuit of claim 9, wherein varying of the frequency and duty cycle of the target pulse signal with a change of the target current further comprises:

under a condition that the target current decreases, the output waveform of the target pulse signal varies in a manner that: the low-level duty cycle becomes smaller, and the high-level duty cycle becomes larger.

11. The current measurement circuit of claim 1, wherein the calculation unit comprises a Field Programmable Gate Array (FPGA), or a Micro Control Unit (MCU), or a moving average calculation unit.

12. The current measurement circuit of claim 1, wherein the sensor unit comprises an equivalent resistance and a parasitic equivalent parallel capacitance of a thin film nanopore.

13. The current measurement circuit of claim 12, wherein the target current is a current flowing through the thin film nanopore during nanopore gene sequencing.

14. A current measurement method realized by the current measurement circuit of claim 1, comprising:

amplifying, by the amplification unit, the electrical signal from the sensor unit;

outputting, by the comparison unit, the high level under a condition that the voltage signal output by the amplification unit is greater than the preset voltage and the low level under a condition that the voltage signal output by the amplification unit is less than the preset voltage, to obtain the initial pulse signal;

delaying, by the delay unit, the output of the initial pulse signal to obtain the target pulse signal;

feeding back, by the resistance unit, the charging and discharging currents to the amplification unit based on the target pulse signal; and calculating, by the calculation unit, the target current based on the target pulse signal output by the delay unit, wherein the target current is the current flowing through the sensor unit, wherein the calculating, by the calculation unit, the target current based on the target pulse signal output by the delay unit comprises:

calculating, by the calculation unit, the target current based on a frequency and a duty cycle of the target pulse signal output by the delay unit; or performing, by the calculation unit, moving average calculation based on the target pulse signal output by the delay unit to obtain a value of the target current.

15. A nanopore sequencing device, comprising the current measurement circuit of claim 1.

* * * * *